(12) United States Patent
Janna

(10) Patent No.: US 11,937,896 B1
(45) Date of Patent: Mar. 26, 2024

(54) ORTHOPEDIC IMPLANTS WITH IMPROVED SENSORS

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventor: Sied W. Janna, Memphis, TN (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 688 days.

(21) Appl. No.: 16/851,408

(22) Filed: Apr. 17, 2020

Related U.S. Application Data

(60) Provisional application No. 62/846,078, filed on May 10, 2019.

(51) Int. Cl.
| | |
|---|---|
| A61B 5/00 | (2006.01) |
| A61B 5/11 | (2006.01) |
| A61B 5/145 | (2006.01) |
| G16H 10/60 | (2018.01) |
| G16H 40/63 | (2018.01) |
| G16H 40/67 | (2018.01) |
| A61B 5/0205 | (2006.01) |
| A61B 5/026 | (2006.01) |

(52) U.S. Cl.
CPC .......... *A61B 5/0031* (2013.01); *A61B 5/1117* (2013.01); *A61B 5/14546* (2013.01); *A61B 5/4094* (2013.01); *A61B 5/6878* (2013.01); *G16H 10/60* (2018.01); *G16H 40/63* (2018.01); *G16H 40/67* (2018.01); *A61B 5/02055* (2013.01); *A61B 5/026* (2013.01); *A61B 5/14539* (2013.01); *A61B 5/4812* (2013.01)

(58) Field of Classification Search
CPC . A61B 5/0031; A61B 5/1117; A61B 5/14546; A61B 5/4094; A61B 5/6878; A61B 5/02055; A61B 5/026; A61B 5/14539; A61B 5/4812; G16H 40/67; G16H 10/60; G16H 40/63

See application file for complete search history.

(56) References Cited

U.S. PATENT DOCUMENTS

| | | | |
|---|---|---|---|
| 4,519,401 A | 5/1985 | Ko et al. | |
| 6,034,296 A | 3/2000 | Elvin et al. | |
| 6,628,989 B1* | 9/2003 | Penner | A61N 1/37217 |
| | | | 607/30 |
| 7,918,887 B2* | 4/2011 | Roche | A61B 5/0086 |
| | | | 623/17.11 |

(Continued)

FOREIGN PATENT DOCUMENTS

WO    18001389 A1    1/2018

*Primary Examiner* — Shirley X Jian
(74) *Attorney, Agent, or Firm* — KDW Firm PLLC

(57) ABSTRACT

Systems and methods for power conservation of embedded sensors are provided. In some embodiments, at least one sensor positioned within an orthopedic implant operably senses a triggering event of a patient. A sensor signal representative of the triggering event may be sent from a controller to a processor, wherein the controller is operatively connected to the at least one sensor. A command signal may then be sent from the processor to control operation of the at least one sensor.

20 Claims, 4 Drawing Sheets

(56) References Cited

U.S. PATENT DOCUMENTS

| | | | |
|---|---|---|---|
| 8,372,147 B2 * | 2/2013 | Roche | A61B 5/6846 623/17.11 |
| 8,372,153 B2 * | 2/2013 | Roche | A61B 5/4504 623/20.14 |
| 8,444,654 B2 * | 5/2013 | Roche | A61B 5/0086 606/102 |
| 8,761,859 B2 * | 6/2014 | Roche | A61B 5/1459 600/407 |
| 8,904,214 B2 | 12/2014 | Volpe et al. | |
| 9,451,919 B2 * | 9/2016 | Roche | A61B 5/4528 |
| 10,143,391 B2 | 12/2018 | Damaser et al. | |
| 10,582,891 B2 * | 3/2020 | Wiedenhoefer | A61B 5/6878 |
| 11,020,053 B2 * | 6/2021 | Bailey | A61B 5/0024 |
| 2002/0010390 A1 | 1/2002 | Guice et al. | |
| 2002/0032470 A1 | 3/2002 | Linberg | |
| 2002/0173702 A1 | 11/2002 | Lebel et al. | |
| 2003/0065308 A1 | 4/2003 | Lebel et al. | |
| 2004/0122489 A1 | 6/2004 | Mazar et al. | |
| 2004/0167416 A1 | 8/2004 | Lee | |
| 2006/0224088 A1 * | 10/2006 | Roche | A61B 5/0086 600/595 |
| 2008/0021514 A1 * | 1/2008 | Pless | A61B 5/30 607/45 |
| 2008/0262331 A1 | 10/2008 | Gerber et al. | |
| 2008/0262374 A1 | 10/2008 | Gerber et al. | |
| 2008/0300659 A1 | 12/2008 | Matos | |
| 2009/0076343 A1 | 3/2009 | James et al. | |
| 2009/0312650 A1 | 12/2009 | Maile et al. | |
| 2010/0168829 A1 * | 7/2010 | Schwartz | A61N 1/05 607/116 |
| 2011/0213221 A1 * | 9/2011 | Roche | A61B 5/4528 600/301 |
| 2012/0191151 A1 | 7/2012 | Kameli | |
| 2012/0229299 A1 | 9/2012 | Skoldengen et al. | |
| 2013/0184788 A1 * | 7/2013 | Jager | A61B 5/11 607/62 |
| 2015/0238304 A1 * | 8/2015 | Lamraoui | A61N 1/36007 700/275 |
| 2016/0302721 A1 * | 10/2016 | Wiedenhoefer | A61B 5/1126 |
| 2017/0143261 A1 * | 5/2017 | Wiedenhoefer | A61B 5/0086 |
| 2017/0147789 A1 * | 5/2017 | Wiedenhoefer | A61B 5/02055 |
| 2017/0181698 A1 * | 6/2017 | Wiedenhoefer | A61B 5/112 |
| 2017/0246466 A1 | 8/2017 | Murphy et al. | |
| 2018/0028824 A1 | 2/2018 | Pivonka et al. | |
| 2018/0055547 A1 | 3/2018 | Janna et al. | |
| 2018/0078138 A1 | 3/2018 | Dastgheib et al. | |
| 2018/0368066 A1 | 12/2018 | Howell et al. | |
| 2019/0192072 A1 * | 6/2019 | Bailey | A61B 5/4851 |
| 2019/0350523 A1 * | 11/2019 | Bailey | A61B 5/4851 |
| 2020/0054215 A1 * | 2/2020 | Roche | A61B 5/0031 |
| 2021/0030357 A1 * | 2/2021 | Wiedenhoefer | A61B 5/0015 |
| 2021/0212566 A1 * | 7/2021 | Roche | A61B 5/076 |
| 2021/0290063 A1 * | 9/2021 | Roche | A61B 5/4528 |
| 2021/0290398 A1 * | 9/2021 | Roche | A61B 5/686 |

* cited by examiner

ORTHOPEDIC IMPLANTS WITH IMPROVED SENSORS

CROSS-REFERENCE TO RELATED APPLICATION

This application claims the benefit of U.S. Provisional Patent Application No. 62/846,078, filed May 10, 2019, entitled "Orthopedic Implants with Improved Sensors," the entire contents of which application is hereby incorporated by reference in its entirety.

TECHNICAL FIELD

The present disclosure relates generally to orthopedic implants with embedded sensors and, more particularly, to systems and methods for conserving power and/or updating software in the embedded sensors.

BACKGROUND

Embedding sensing technology into orthopedic implants or devices is known. In some cases, sensors implanted within the implant can monitor and communicate conditions within the body without invasive investigation. For example, positioning strain gauges within an implant can be used to monitor bone recovering, wherein strain gauges can communicate the load on the implant, which can be monitored to determine proper healing. Monitoring a patient's body temperature, PH level, etc., can be used to monitor for the possibility of an infection. These are just some examples of the physiological properties that can be monitored within a patient's body. In use, knowledge of various patient properties can be important to the patient and health care provider in terms of, for example, rehabilitation, potential secondary treatment, and determining the optimal time to return to work. In various embodiments, patient properties can be monitored in real-time using an array of implantable sensors embedded within an orthopedic implant.

Approaches for incorporating sensors in an orthopedic implant face numerous challenges including, for example, providing sufficient power to the embedded sensor(s) for the sensor(s) to operate over the lifespan of the implant, which could be years or decades. In addition, the software in the embedded sensor(s) may need updating. If necessary, a re-implantation procedure may need to be performed if replacement of the sensor or battery is needed, thus increasing discomfort and risk to the patient.

For these reasons among others, a need remains for further improvements in this technological field. The present disclosure addresses this need.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides systems and methods for sensing a triggering event with at least one sensor, wherein the triggering event may be a sudden acceleration or deceleration, a change in environment, sleeping, seizure, death, a change in blood flow, a change in blood pressure, a change in compartment pressure, and/or a change in proximity to home base. Various sensors may sense acceleration, temperature, sound, infrared, pressure, pH, salinity, sodium, calcium, protein, bio markers, and/or a radio signal. In some embodiments, the triggering event may be passage of a predetermined amount of time and/or based on a preference. The method may further include sending a sensor signal from a controller to a processor, wherein the controller is operatively connected to the at least one sensor, and sending a command signal from the processor to manage power usage by the at least one sensor.

In some embodiments, the processor is remote from the controller. In some embodiments, the processor initiates a communication subroutine, and the communication subroutine generates a message to send to an address. In some embodiments, the message may be in the form of an email or text. In some embodiments, the address may be an email address or telephone number for a recipient.

In some embodiments, the recipient is a health care provider (HCP) or a patient. In some embodiments, the recipient may reply with a message. In some embodiments, the message may be instructions. In some embodiments, the message may be an inquiry. In some embodiments, the inquiry may be a request for approval.

In some embodiments, the command signal turns on and off a plurality of sensors. In some embodiments, the command signal may initiate a communication protocol via the controller to turn on and off one or more of the sensors. In some embodiments, the communication protocol may include near field communication (NFC). In other embodiments, the communication protocol may include cellular data. In some embodiments, the command signal may turn on a transmitter/transceiver (used interchangeably herein without the intent to limit), wherein the transceiver connects to a mobile computing device, and wherein the mobile computing device transmits the email or text.

In some embodiments, the sensor may be operatively connected to or embedded within an orthopedic implant. In some embodiments, the processor may initiate a data download, which is stored in memory. In some embodiments, the processor sends instructions to the controller. In some embodiments, the processor analyzes the data and the controller selectively turns off one or more sensors that are not providing data or that are only providing noise. In some embodiments, the processor may analyze the data and the controller reverts to a main sensor unless and until a triggering event. In some embodiments, the processor may analyze the data to determine whether a patient has achieved a steady state. When the patient has achieved a steady state, the processor may send a signal to the controller to turn off one or more of the sensors.

In some embodiments, a method may include providing a first sensor and a second sensor each associated with an orthopedic implant and a controller, wherein each of the first sensor and the second sensor includes an internal power source, and providing the internal power source of the first sensor in an active mode and the internal power source of the second sensor in a standby mode. The method may further include detecting, by the first sensor, a triggering event, and activating, in response to the triggering event, the internal power source of the second sensor from the standby mode. The method may further include detecting, by the second sensor, a characteristic associated with the orthopedic implant.

In some embodiments, a system may include a first sensor and a second sensor associated with one or more orthopedic implants, and a processor operable to receive a sensor signal from the first sensor in response to a triggering event. The system may further include a first internal power source of the first sensor and a second internal power source of the second sensor, and a controller associated with the first sensor and the second sensor, wherein the controller is operable to receive a command signal from the processor. The command signal is operable to activate the second internal power source of the second sensor from a standby mode, and detect, by the second sensor, a characteristic of the one or more orthopedic implants.

In some embodiments, a method may include providing a first sensor and a second sensor each associated with a controller and one or more orthopedic implants, wherein the first sensor includes a first internal power source, and wherein the second sensor includes a second internal power source. The method may further include providing the first internal power source in an active mode and the second internal power source in a standby mode, and detecting, by the first sensor, a triggering event. The method may further include delivering, from the first sensor, a sensor signal to a processor in response to the triggering event, activating, in response to a command signal from the processor, the second internal power source of the second sensor from the standby mode, and detecting, by the second sensor, a characteristic of the one or more orthopedic implants.

Embodiments of the present disclosure provide numerous advantages. For example, managing power consumption leads to a longer life of implanted sensors. Furthermore, algorithms, both simple and complex, manipulate sensor data to provide the caregiver meaningful information from a trove of data. As algorithms are developed and optimized, the implant sensor electronics may be updated as appropriate. Still furthermore, by discriminately controlling a transceiver of the implant, the sensor electronics operating system (SEOS) may be updated for optimized function and power management.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

By way of example, embodiments of the disclosed device will now be described, with reference to the accompanying drawings, in which.

Figure 1:
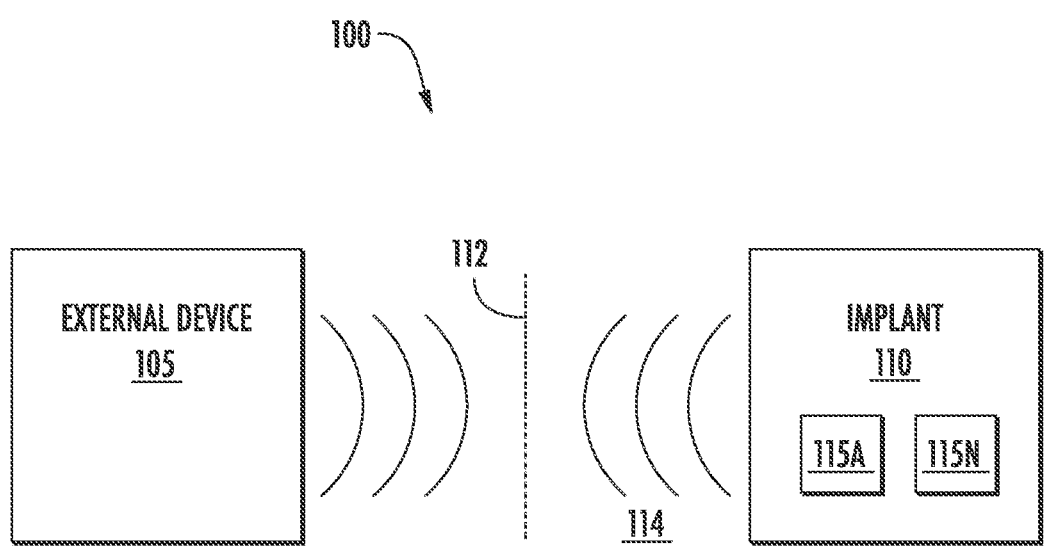
FIG. 1 is a diagrammatic representation of a sensor system in accordance with embodiments of the disclosure.

The drawings are not necessarily to scale. The drawings are merely representations, not intended to portray specific parameters of the disclosure. The drawings are intended to depict example embodiments of the disclosure, and therefore are not be considered as limiting in scope. In the drawings, like numbering represents like elements.

Furthermore, certain elements in some of the figures may be omitted, or illustrated not-to-scale, for illustrative clarity. Furthermore, for clarity, some reference numbers may be omitted in certain drawings.

DETAILED DESCRIPTION

Embodiments of an improved method and system for reduced power consumption of implanted sensors will now be described more fully hereinafter with reference to the accompanying drawings, in which preferred embodiments of the present disclosure are presented. As will be described and illustrated, in some embodiments, conditions in and around the body can be sensed and communicated using a sensor system. Unlike prior art embedded sensors, which are powered inductively and have limited functionality, i.e., to provide raw sensor data to a data collection device, the implanted sensor system of the present disclosure can be controlled automatically, or based on caregiver instructions, as a result of an event, preference, and/or time.

As will be described and illustrated, in some embodiments, the sensor system may include at least one implantable sensor, such as a strain gauge, accelerometer, gyrometer, inertial sensor, etc. The sensor may be operatively associated with an orthopedic implant (e.g., embedded within, coupled to, or the like). The sensor system may further include an internal power source, such as a battery or energy scavenging system/capacitor/battery, a processor including an operating system, and an external device that can communicatively couple with the sensor system, such as a computer, tablet, phone, etc. Furthermore, the sensor system may include software capable of providing data to the caregiver and can communicating changes to an operating system of the sensor system.

In addition, and/or alternatively, as will be described and illustrated, in some embodiments, the sensor system may include multiple sensors, autonomous switching on and off sensors based on events, timing, and predictive performance increases, such as switching sensors on when the threat of an event occurs. For example, an inertial motion sensor might detect a patient falling, which would cause one or more sensors to become active to record data and process the data along with ensuing post-fall data to determine the severity of the fall and its consequences, contacting the clinician if necessary. In one non-limiting embodiment, one primary sensor may stay on at all times, while the other sensors are in a low-power or standby mode. An event (e.g., patient action, clinician remotely initiates monitoring via mobile phone, or at a specific interval) detected by the main sensor, may then trigger the other sensors to turn on or become active, and provide data to a healthcare provider.

Referring to FIG. 1, a non-limiting example embodiment of a sensor system (hereinafter "system") 100 is illustrated. As shown, the system 100 may include one or more external devices 105 in wireless communication with an implantable orthopedic device or implant (hereinafter "implant") 110. In use, as will be appreciated by one of ordinary skill in the art, the implant 110 may be implanted into a patient's body. The external device 105 may communicate with the implant 110 through the skin 112 of the patient 114.

The external device 105 may be any device capable of wirelessly communicating with the implant 110, such as a computer, a mobile device, a personal data assistant, a patient programmer, or the like. In some embodiments, the external device 105 is monitored and controlled by a health care provider (HCP). In other embodiments, the external device 105 may be in possession of the patient 114. In yet other embodiments, in which more than one external device 105 are in communication with the implant 110, both the patient 114 and the HCP may be in possession of external devices 105. It will be appreciated that the external device 105 and the implant 110 may be capable of one-way or two-way communication.

Although not shown in detail for the sake of brevity, the external device(s) 105 may include various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments herein are not limited in this context.

The implant 110 may be a "smart implant" incorporating one or more sensors capable of sensing patient properties, circuitry for applying intelligence to determine whether action is required, and acting on the sensed information in a controlled, beneficial manner. In various embodiments, the implant 110 may be an intramedullary nail, a bone plate, a bone screw, an external fixation device, a joint product, a knee replacement device, a hip replacement device, a trauma product, a spine product, or an interference screw. Although only one implant 110 is shown, it will be appreciated that the system 100 may include multiple implants 110 in communication with the external device 105 and/or one another. Embodiments herein are not limited in this context.

In various embodiments, the implant 110 carries out patient monitoring methods, or portions thereof, described herein. In some other embodiments, the combination of the implant 110 and the external device 105 carry out the various patient monitoring methods, or portions thereof. For example, the implant 110 may not include an internal processor. Instead, processing can be performed by the external device 105. Embodiments herein are not limited in this context.

As shown, the implant 110 may include one or more sensors 115A-115N embedded within or attached thereto. The sensors 115A-115N may be any device capable of detecting, obtaining, or the like, information regarding the implant 110, the patient 114, etc. As will be described in greater detail below, the sensors 115A-115N may be any type of sensor capable of sensing one or more patient properties such as, for example, acceleration, temperature, sound, infrared, pressure, pH, salinity, sodium, calcium, protein, bio markers, radio signals, respiration, electrocardiogram (ECG) feedback, blood oxygen levels, heartbeat, audio, GPS locators, magnetic field, etc. In these embodiments, the sensors 115A-115N may have a relatively low sampling rate, such as wireless sensors. Although only two sensors 115A-115N are shown, it will be appreciated that the system 100 may include a greater or lesser number of sensors in communication with the external device 105, other implants, and/or one another. Embodiments herein are not limited in this context.

Figure 2:
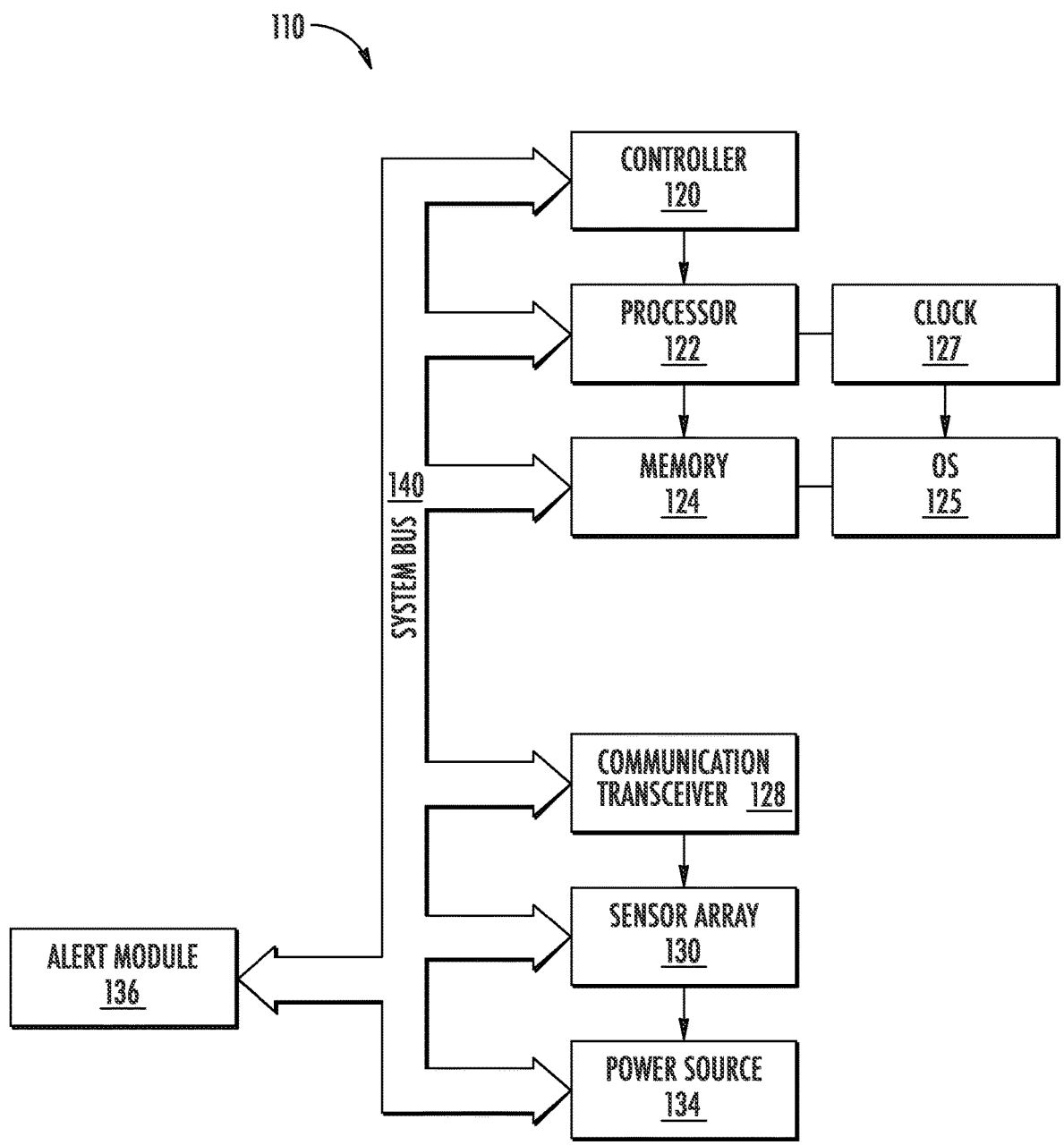
FIG. 2 is a schematic block diagram of an example implantable device of the sensor system of FIG. 1 in accordance with embodiments of the disclosure.

Turning now to FIG. 2, a non-limiting embodiment of the implant 110 will be described in greater detail. It will be understood that the components shown in FIG. 2 are but one non-limiting example of components that implant 110 may have, and that many other device or system configurations may be employed to carry out the methods described herein. As shown, the implant 110 may include a controller 120 in communication with a processor 122, and memory 124 having an operating system (OS) 125 stored thereon or connected therewith. In some embodiments, the OS 125 is a sensor electronics operating system (SEOS). In some embodiments, the processor 122 is remote from the controller 120. For example, the processor 122 may be part of the external device 105 (FIG. 1) or a different device.

In the non-limiting embodiment shown, the components of the implant 110 may be connected by any suitable mechanism now known or hereafter developed. For example, as shown, the components of the implant 110 may be connected to a bi-directional data bus 140. In some embodiments, all components of the implant 110, except the power source 134, can be configured on one or more Application Specific Integrated Circuits (ASICs) or may be one or more discrete components, or a combination of both.

The implant 110 may further include a communication transceiver 128, a sensor or sensor array 130, and a power source 134, such as a battery, for providing power to the sensor array 130. It is appreciated that the battery capacity, runtime, and type (e.g., lithium ion, nickel-cadmium, or nickel-metal hydride) can be changed to best fit the specific application of the implant 110 and/or sensor array 130.

It should be appreciated that the sensor array 130 may include sensors 115A-114N, as discussed above with regard to FIG. 1, and may include other components for transmitting sensed information to and from the controller 120, the processor 122, and/or memory 124. In some embodiments, the sensor array 130 may include one or more analog to digital converters to convert analog signals generated by the sensors 115A-114N into digital signals usable by the processor 122, as well as suitable filter and amplifier circuitry not shown.

In some embodiments, the controller 120 can be configured to automatically control power provided to the sensor array 130 by the power source 134. In various embodiments, the controller 120 may be implemented using hardware or a combination of hardware and software. For instance, in one embodiment, the controller 120 is implemented as a software component that is stored within memory 124 and executed by the processor 122. In this embodiment, the instructions included in the controller 120 may program the processor 122 to control power consumption of the sensor array 130 in response to a recognized triggering event. In other embodiments, the controller 120 can be an ASIC that is coupled to the processor 122 and tailored to control power consumption of the sensor array 130 in response to the recognized triggering event. Embodiments of the controller 120 are not limited to a particular hardware or software implementation.

In some embodiments, the processor 122 initiates a communication subroutine in response to the triggering event, wherein the communication subroutine may generate a message to send to an address. For example, the message may be in the form of an email or text, which may be sent to the external device 105. More specifically, in some embodiments, the communication subroutine may turn on the communication transceiver 128, which then connects to the external device 105. The external device 105 may be a mobile device containing an application operable to transmit the email or text to a second external device, such as a computer operated by the HCP. In other embodiments, the communication transceiver 128 may connect first to the external device 105 of the HCP, and then transmit an email or text to a second external device, such as a mobile device of the patient 114. In some embodiments, the reply message comprises instructions for the patient 114, wherein the instructions may be generated automatically based on the triggering event. Some non-limiting examples may include, "contact your healthcare provider for instructions," "begin recording your daily activities," or "seek immediate medical attention." In some embodiments, the message may comprise an inquiry, such as a request for approval. One non-limiting example may include, "a triggering event has occurred, should the predetermined sensors be activated?" Another non-limiting example may include, "a triggering event has occurred. Are you ok? Reply Y/N."

In some embodiments, the command signal may turn on and off one or more sensors of the sensor array 130 via the controller 120. As used herein, sensors that are in a standby or low-power mode may be considered "off." Activation of the one or more sensors of the sensor array 130 may transition the sensors from the low-power or standby mode to the active/full-power mode. The command signal may be delivered according to a variety of non-limiting communication protocols. For example, the communication protocol may include near field communication, radio frequency identification (RFID), cellular data, Bluetooth®, and the like. In some embodiments, the command signal turns on the communication transceiver 128. The communication transceiver 128 may then communicate with the external device 105, which may be a mobile device operable to transmit the email or text to a second external device, such as a computer operated by the HCP.

As used herein, a recognized triggering events may occur upon a deviation from any number of physiological, pathological and/or environmental predetermined thresholds. Various non-limiting examples of triggering events may include acceleration or deceleration, a change in environment, a sleep state, seizure, death, a change in blood flow, a change in blood pressure, a change in compartment pressure, a change in a proximity to a home base (e.g., a respirator, an IV, a wheelchair, etc.), a change in temperature, a detected sound, a change in infrared measurements, a change in pressure, a change in pH, a change in salinity, a change in sodium, a change in calcium, a change in protein, recognition of one or more bio markers, and/or a change in radio signal.

In some embodiments, the triggering event may occur upon the passage of a predetermined amount of time. For example, at a certain time every hour, day or week, the sensor array 130 and the communication transceiver 128 may be turned on for data collection and transmission. In some embodiments, a clock 127 may count the number of seconds, minutes, hours, etc., since a fixed point in time. Based on the passage of a predetermined interval of time, a command signal from the processor 122 may turn on one or more sensors of the sensor array 130 via the controller 120. Another command signal from the processor 122 may subsequently turn off one or more sensors of the sensor array 130 via the controller 120.

In other embodiments, the triggering event is based on a preference of the patient 114 and/or the HCP. For example, the patient 114 and/or the HCP may select the type of patient metric that will cause a triggering event, or may select threshold values for establishing the occurrence of the triggering event.

In yet other embodiments, the triggering event is a request by the patient 114 and/or the HCP. For example, the patient 114 or the HCP can cause one or more sensors of the sensor array 130 to be turned on for data collection, transmission, and analysis. In some embodiments, the patent 114 may operate a mobile device application, which allows the patient to activate sensors, respond to alerts, transmit data to the HCP, communicate with the HCP via e-mail or text, etc. For example, the patient or HCP may desire to turn on the sensors to monitor certain properties after a workout or physical therapy session, or the like.

The processor 122 may be synchronous and typically operates on low power, such as a synthesized core operating with a compatible instruction set. The processor 122 can perform a series of instructions that result in manipulated data stored in and retrieved from the memory 124. The processor 122 may be any type of processor, multi-processor or controller, whether commercially available or specially manufactured. In some embodiments, the processor 122 can comprise two or more processors and/or two or more processor cores (e.g., processor able to execute multiple processing strings or threads in parallel and/or intermittently). At least some of these processors and/or processor cores can be configured to execute the operating system 125.

In some embodiments, memory 124 includes memory sufficient for operation of implant 110, such as volatile Random Access Memory (RAM) for example static RAM, nonvolatile Read Only Memory (ROM), Electrically Erasable Programmable Read Only Memory (EEPROM) for example Flash EEPROM, and register arrays configured on ASICs.

The communication transceiver 128 or other wireless module provides for communication between the implant 110 and the external device 105 (FIG. 1). Communication may be bi-directional or unidirectional. Furthermore, the communication transceiver 128 may be part of a telemetry module further including a telemetry antenna, a receiver, and a telemetry processor. It will be understood that other forms of wireless communication may readily be substituted where appropriate for telemetry. Examples of other communication forms may include Bluetooth®, 802.11, near field communication (NFC) and radio frequency (RF). RF is a wireless communication technology using electromagnetic waves to transmit and receive data using a signal above approximately 0.1 MHz in frequency. Due to size and power consumption constraints, the controller 120 may utilize the Medical Implantable Communications Service (MICS) in order to meet certain international standards for communication. MICS is an ultra-low power, mobile radio service for transmitting data in support of diagnostic or therapeutic functions associated with implanted medical devices. The MICS permits individuals and medical practi-tioners to utilize ultra-low power medical implant devices, without causing interference to other users of the electromagnetic radio spectrum.

The implant 110 may further include a timer or clock 127 operable with the processor 122. The clock 127 may count the number of seconds since a fixed date for date/time stamping of events and may be used for patient monitoring and/or therapy control. For example, the controller 120 may activate and/or deactivate one or more sensors of the sensor array 130 at an appropriate time and based on information from the clock 127.

Although not shown, the implant 110 can also optionally include several system interface components, such as a network interface, and a sensor system interface. Each of these interface components can be configured to exchange data with one or more components of the implant 110 and/or the external device 105. The components used by the interfaces of the implant 110 can include hardware components, software components, or a combination of both. Physical and logical coupling by the interface components enables the controller 120 to communicate with and/or, in some instances, power or control the operation of the sensor array 130.

Optional alert module 136 may issue an alert via the external device 105, e.g., an audible alert or tactile alert, such as a vibration. An alert may be issued if information indicative of an event is detected. The alert may serve to prompt the HCP or the patient 114 to respond to the triggering alert, e.g., by seeking medical attention and/or communicating additional feedback. Embodiments herein are not limited in this context.

As described above, one or more sensors of the sensor array 130 may be operable to detect changes in temperature in proximity to the implant 110. For example, the temperature of body tissue at a site of infection is generally greater than that of body tissue at a location removed from the site of infection. Accordingly, an increase in temperature in proximity to the implant 110 may serve as an indicator of infection. Any suitable sensor capable of detecting temperature or changes in temperature may be employed. For example, the sensor array 130 may include a thermocouple, a thermistor, a junction-based thermal sensor, a thermopile, a fiber optic detector, an acoustic temperature sensor, a quartz or other resonant temperature sensor, a thermo-mechanical temperature sensor, a thin film resistive element, or the like.

In some embodiments, one or more sensors of the sensor array 130 may be operable to detect changes in impedance in proximity to the implant 110. For example, an increase in fluid in tissue may be observed. Accordingly, a decrease in impedance of tissue in proximity may serve as an indicator of infection, for example. In the case of impedance measurement, the sensor array 130 may include one or more electrodes, wherein impedance may be measured between two electrodes. During operation, current or voltage may be applied between the electrodes, with one electrode at any given time serving as a source and the other serving as a sink. In various embodiments, the electrodes may be positioned at different positions in and around the implant 110.

In some embodiments, one or more sensors of the sensor array 130 may be operable to detect changes in pH in proximity to the implant 110. As pH may serve as a general indicator of the state of a tissue, a change in pH may be indicative of infection. Any suitable sensor capable of detecting pH or changes in pH may be employed in the implant 110.

In some embodiments, one or more sensors of the sensor array 130 may be operable to detect biological markers. Non-limiting examples of biological markers of infection include viral, fungal, or bacterial proteins or nucleic acids or fragments thereof. As most infections associated with implantable medical devices appear to be due to infection due to *Staphylococcus aureus, Staphylococcus epidermis, Pseudomonus auruginosa* and *Candidia* Sp., detection of proteins, nucleic acids, or fragments thereof of such microorganisms may be beneficial.

Any sensor capable of detecting such biological markers indicative of infection may be used. In various embodiments, biosensors may be used to detect the presence of a molecule in proximity to the implant 110. Any known or future developed biosensor may be used. The biosensor may have, e.g., an enzyme, an antibody, a receptor, or the like operably coupled to, e.g., a suitable physical transducer capable of converting the biological signal into an electrical signal. In some situations, receptors or enzymes that reversibly bind the molecule being detected may be preferred. In various embodiments, one or more sensors of the sensor array 130 includes an electrode with an ion selective coating that is capable of directly transducing the amount of a particular substance.

Alternatively, detection of indicators of an immune response may be detected. For example, an increase in a pro-inflammatory cytokine. Non-limiting examples of proinflammatory cytokines include tumor necrosis factor (TNF; also known as TNFα or cachectin), interleukin (IL)-1α, IL-10, IL-2; IL-5, IL-6, IL-8, IL-15, IL-18, interferon γ (IFN-γ); platelet-activating factor (PAF), thromboxane; soluble adhesion molecules; vasoactive neuropeptides; phospholipase A2; plasminogen activator inhibitor (PAI-1); free radical generation; neopterin; CD14; prostacyclin; neutrophil elastase; protein kinase; monocyte chemotactic proteins 1 and 2 (MCP-1, MCP-2); macrophage migration inhibitory factor (MIF), high mobility group box protein 1 (HMGB-1), and other known factors. Indication of an immune response may also be detected by a decrease in an anti-inflammatory cytokine in proximity to the implant 110. Non-limiting examples of anti-inflammatory cytokines include IL-4, IL-10, IL-17, IL-13, IL-1α, and TNFα receptor. It will be recognized that some of proinflammatory cytokines may act as anti-inflammatory cytokines in certain circumstances, and vice-versa. Such cytokines are typically referred to as pleiotropic cytokines.

In some embodiments, one or more sensors of the sensor array 130 may be operable to detect an immune response by measuring changes (e.g., baseline versus after device implant or other event, a first point after device implant or other event versus a second point after device implant or other event, etc.) in the presence of other factors involved in an immune response. Non-limiting examples of such other factors include TGF, PDGF, VEGF, EGF, FGF, I-CAM, and nitric oxide. In addition, an immune response may be detected by changes in chemokines, such as 6cKine and MIP3beta, and chemokine receptors, including CCR7 receptor. Further, an immune response may be measured by changes in immune cell population (upregulated Langerhans cells, dendritic cells, lymphocytes), or immune cell surface co-stimulatory molecules (Major Histocompatibility, CD80, CD86, CD28, CD105). An immune response may also be detected by measuring changes in other factors involved in the inflammatory cascade, for example in the signal transduction cascades including factors such as NFκ-B, Egr-1, Smads, toll-like receptors, and MAP kinases. In addition, an immune response may be detected by a change in the presence of an exogenous antigen believed to have caused an inflammatory response, such as, e.g., a bacteria, a virus, or a fungus.

In some embodiments, one or more sensors of the sensor array 130 may be operable to detect a strain or force associated with the implant 110. For example, the sensor array 130 may include one or more sensors capable of measuring mechanical strain, such as a foil or a strain gauge. For example, the implant 110 may be an intramedullary nail, and the sensor array 130 may measure strain on the nail as the load is applied. The sensed data may be downloaded to memory 124 and processed by the processor 122. In this example, the sensed data may be compared to previous measurements. For example, measurements may be taken at predetermined time periods, such as daily or weekly, to determine if a fracture is healing.

The sensor array 130 may further include one or more sensors capable of measuring acceleration or deacceleration of the implant 110. For example, one or more accelerometers may be employed to determine a level of activity, number of steps taken, indication of falling, or a relatively sedentary period. Although non-limiting, raw acceleration or change in relative acceleration of the implant 110 can be determined using a MEMS (micro-electromechanical system) or non-MEMS based accelerometer in a cantilever beam configuration or other relevant configuration (spring-mass-damper), gravimeter, vibrating beam, and/or gyroscope. The accelerometer may be analog or digital with any numbers of axes including a maximum swing of ±50 g. The sensitivity of the accelerometers is sufficient to capture the acceleration data such that when amplified the data is recognizable and discernable (e.g. 0.0001-100 mV/g). The accelerometers bandwidth is suitable to ensure proper data generation and capture (e.g. 0.01-20000 Hz).

The sensor array 130 may further include one or more sensors capable of indicating range of motion of a limb that the implant 110 could be implanted within. For example, a gyrometer or gyroscope can include at least one of a MEMS device and a three-axis device, which can output a signal indicative of an orientation of the implant 110.

Figure 3:
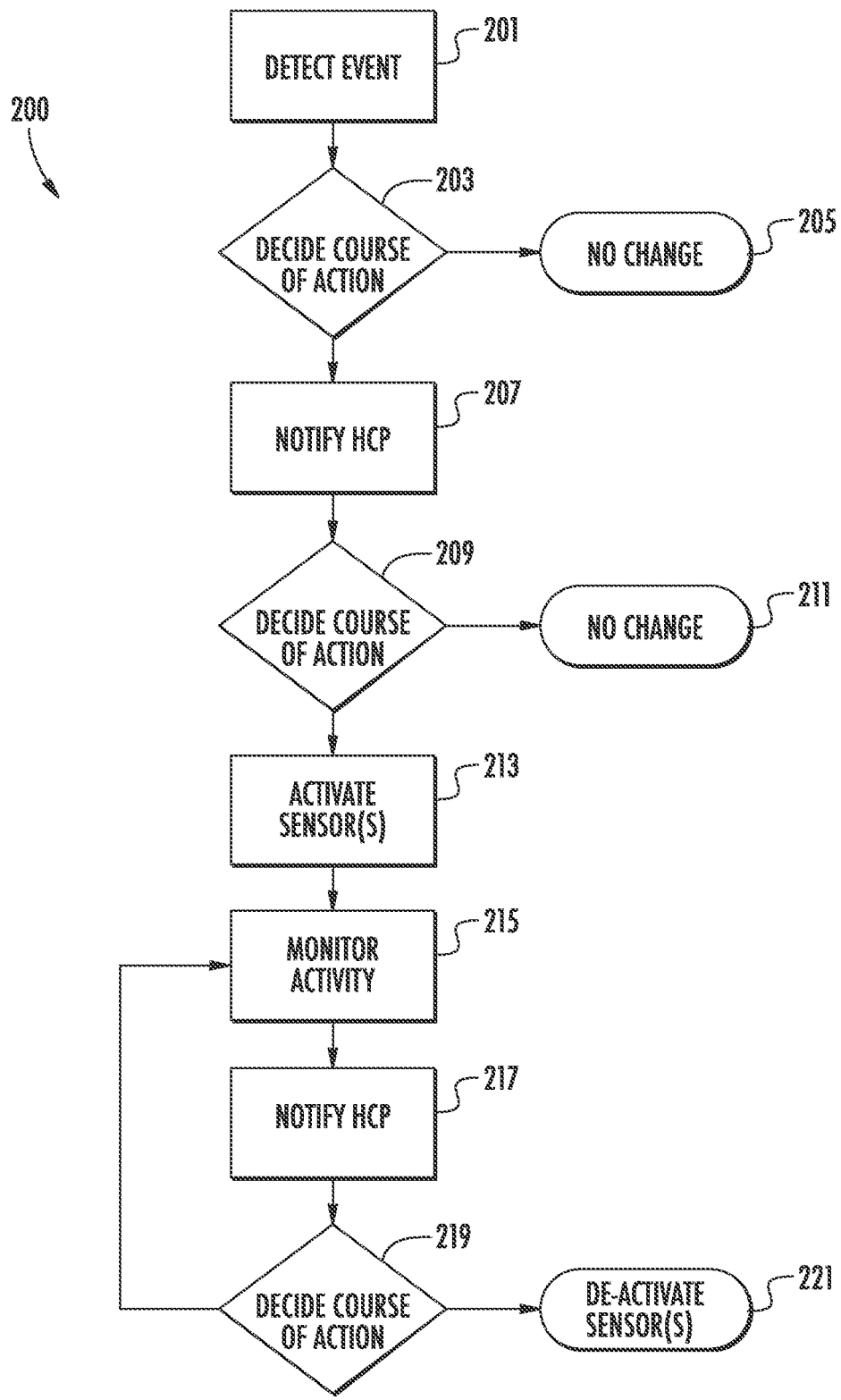
FIG. 3 depicts a method in accordance with embodiments of the disclosure.

Referring to FIG. 3, a non-limiting example embodiment of logic flow 200 is illustrated. The logic flow 200 may be representative of some or all of the operations executed by one or more embodiments described herein. For example, the logic flow 200 may include some or all of the operations performed by the sensor system 100 and implant 110 shown in FIGS. 1-2. Embodiments are not limited in this context.

As shown, at block 201, an event may be detected. As described above, the event may be a triggering event, including but not limited to a request from the patient or HCP, a predetermine time of day or week, a fall, sudden acceleration or deceleration, a change in environment, sleeping, seizure, death, a change in blood flow, a change in blood pressure, a change in compartment pressure, a change in temperature, a change in impedance, and/or a proximity to a home base. In some embodiments, the event may be detected using one or more sensors of the sensor array 130 operating with the processor 122 and the controller 120. For example, a sensor signal may be sent from the controller 120 to the processor 122, wherein the controller 120 is operatively connected to one or more sensors of the sensor array 130. Although non-limiting, the sensor(s) of the sensor array 130 may sense acceleration, temperature, sound, infrared, pressure, pH, salinity, sodium, calcium, protein, bio markers, and/or a radio signal.

In some embodiments, only a subset of the sensors of the sensor array 130 may initially be on/active to detect the triggering event. For example, if the patient 114 is deemed a falling risk, an accelerometer of the sensor array 130 may remain on to detect when the patient makes a sudden movement, as during a fall. Should the triggering event occur, one or more additional sensors of the sensor array 130 may then be switched on to further observe the patient 114. For example, the triggering event may turn on a gyrometer or inertial sensor of the sensor array 130 to monitor the orientation of the implant 110 and/or patient 114 to confirm whether a fall has occurred.

At block 203, a course of action is decided/determined. For example, the processor 122 may compare data associated with the event to data stored within memory 124 to determine if a deviation beyond an acceptable limit has been reached. If no action is to be taken, as shown at block 205, the implant 110 may continue to wait for a triggering event. If a course of action has been triggered, an HCP may be notified, as shown at block 207. In some embodiments, a command signal may be sent from the processor 122, wherein the processor 122 may initiate a communication subroutine. For example, the communication subroutine may transmit a signal to the external reader, wherein generates an e-mail or text message to send to an address, such as an email address or telephone number for the HCP.

At block 209, a course of action is decided/determined. For example, the command signal from the processor 122 may turn on one or more sensors of the sensor array 130 via the controller 120, as shown at block 213. In an alternative embodiment, the determination may be made by the external device 105, wherein sensed information may be provided to the external device 105 via the communication transceiver 128.

In some embodiments, the sensor(s) may be turned on in response to a reply message from the HCP, the message including instructions and/or an inquiry, including a request for approval. For example, the HCP may activate the sensor(s) of the sensor array 130 using a mobile phone application connected to the OS 125 of the implant 110 and/or base station periodically tethered to the implant 110.

The reply message may include or trigger a command signal, which initiates a communication protocol via the controller 120. Although not limited to any particular type, the communication protocol may include NFC, RFID, cellular data, Bluetooth®, and the like. In some embodiments, the command signal may turn on the communication transceiver 128. The communication transceiver 128 may then connect to the external device 105.

If no action is to be taken, as shown at block 211, the implant 110 may continue to wait.

At block 215, activity of the patient 114 and/or the sensor(s) of the sensor array 130 may continue to be monitored. In some embodiments, the sensor(s) of the sensor array 130 may continue to sense acceleration, temperature, sound, infrared, pressure, pH, salinity, sodium, calcium, protein, bio markers, and/or a radio signal. However, when only a subset of the sensors of the sensor array 130 have been turned on, only those corresponding sensed characteristics may continue to be monitored.

As shown at block 217, activity of the patient 114 and/or the sensor(s) of the sensor array 130 may then be delivered to the HCP. At block 219, a course of action is decided/determined. For example, the command signal from the processor 122 may turn off one or more sensors of the sensor array 130 via the controller 120, as shown at block 221. In an alternative embodiment, the determination may be made by the external device 105 (FIG. 1), wherein sensed information may be provided to the external device 105 via the communication transceiver 128.

In some embodiments, the processor 122 may initiate a data download, storing the data in memory 124. For example, the processor 122 may compare the activity results of the patient 114 and/or the sensor(s) of the sensor array 130 to one or more threshold values may be retrieved from memory 124. In one non-limiting embodiment, the processor 122 may analyze the data to determine whether the patient 114 has achieved a steady state. In this case, the processor 122 may send instructions to the controller 120 to turn off one or more sensors of the sensor array 130 previously turned on (block 213). In some embodiments, the controller 120 may selectively turn off one or more sensors that are not providing data or only providing noise. In yet other embodiments, the processor 122 may analyze the data, causing the controller 120 to revert to a main sensor unless and until a triggering event again occurs.

In the case the patient has not reached a steady state, the decided course of action at block 219 is to continue to monitor the activity of patient 114 and/or the sensor(s) of the sensor array 130.

Figure 4:
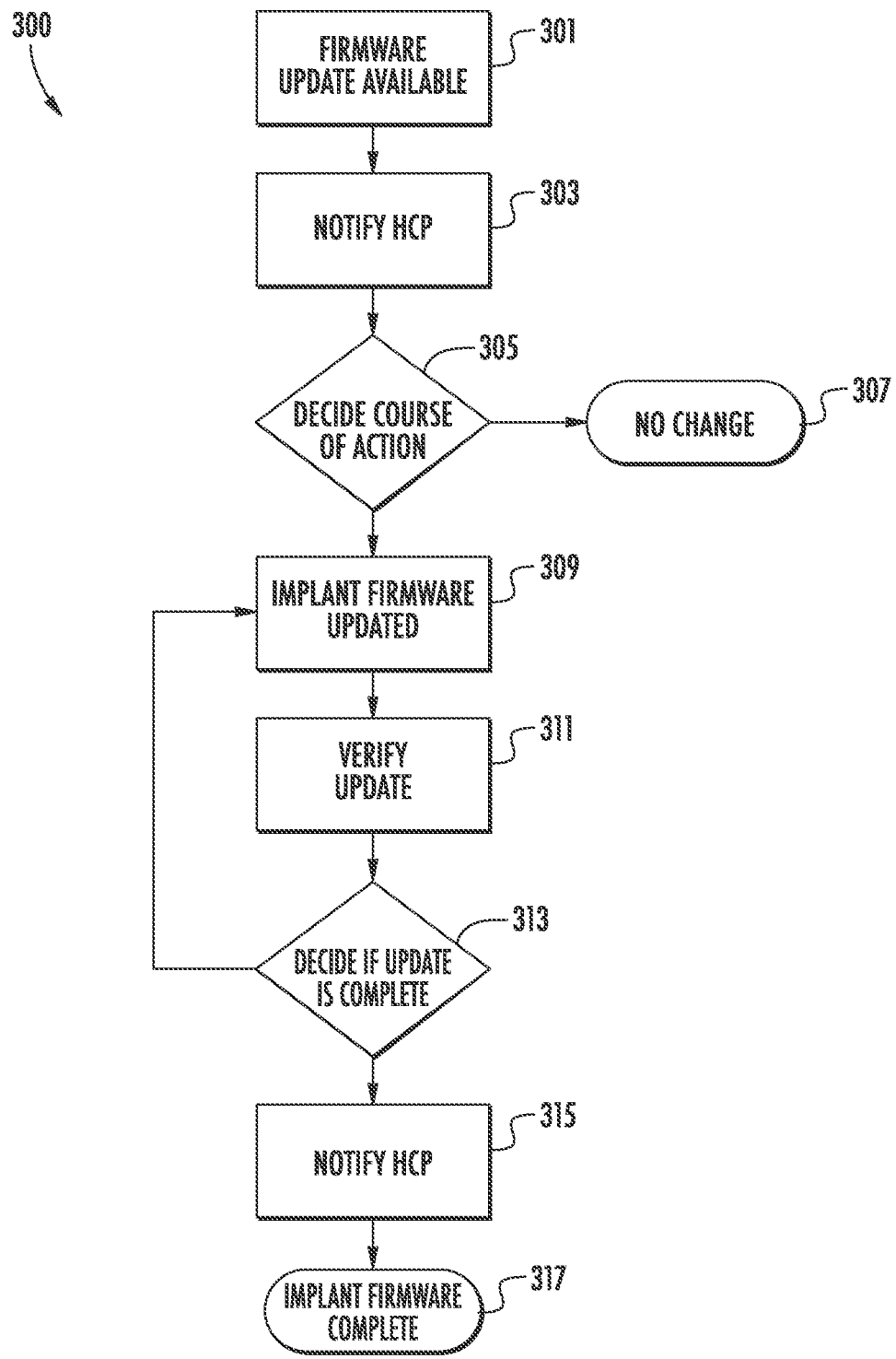
FIG. 4 depicts a method in accordance with embodiments of the disclosure.

Referring to FIG. 4, a non-limiting example embodiment of logic flow 300 for updating the implant sensor electronics as algorithms are developed and optimized is illustrated. The logic flow 300 may be representative of some or all of the operations executed by one or more embodiments described herein. For example, the logic flow 300 may include some or all of the operations performed by the sensor system 100 and implant 110 shown in FIGS. 1-2. Embodiments are not limited in this context.

At block 301, availability of a firmware update is determined or recognized. In some embodiments, the operating system 125 monitors for firmware updates. At block 303, the HCP may be notified of the availability of the firmware update. In some embodiments, the operating system 125 monitors the firmware update and initiates notification of the HCP. At block 305, a determination is made regarding a course of action (e.g., whether or not to update firmware). For example, a firmware update may be needed for any number of reasons including, but not limited to, correcting nefarious or erroneous code, and/or updating the operating system 125 of the implant 110 for optimized function and power management.

If the determination is made not to update the firmware, then no change to the implant 110 is made, as shown at block 307. If the determination is made to update the firmware, the communication transceiver 128 of the implant 110 may be turned on to begin receiving the updated firmware, as shown at block 309. Next, verification of the update may be made by the operating system 125 at block 311, and a determination is made by the operating system 125 whether or not the update is complete, as shown at block 313. In the case the update is not yet complete, the update may continue at block 309. In the case the update is determined to be complete, notification may be made to the HCP, as shown at block 315, and the firmware update is complete (block 317).

While the present disclosure refers to certain embodiments, numerous modifications, alterations, and changes to the described embodiments are possible without departing from the sphere and scope of the present disclosure. Accordingly, it is intended that the present disclosure not be limited to the described embodiments, but that it has the full scope. The discussion of any embodiment is meant only to be explanatory and is not intended to suggest that the scope of the disclosure is limited to these embodiments. In other words, while illustrative embodiments of the disclosure have been described in detail herein, it is to be understood that the inventive concepts may be otherwise variously embodied and employed.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations.

As used in this application, the terms "system" and "component" and "module" are intended to refer to a computer-related entity, either hardware, a combination of hardware and software, software, or software in execution, examples of which are provided by the exemplary system 100. For example, a component can be, but is not limited to being, a process running on a computer processor, a computer processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

It will be further understood that a computer readable medium containing instructions that when implemented cause an implantable medical device (or system including an implantable medical device) to perform the methods described herein are contemplated. In an embodiment the computer readable medium contains instructions that when implemented cause an implantable medical device to (i) detect a first event associated with the implanted medical device; (ii) activate a sensor module of the implanted medical device at or after the detection of the first event, the sensor module capable of detecting further indicators of the patient; (ii) deactivate the sensor module at some future time after the sensor module is activated; and (iii) determine whether information regarding the indicator requires further action, e.g., by a HCP. Devices including the computer readable medium are also contemplated. The computing system 100 generally is configured to implement all logic, systems, methods, apparatuses, and functionality described herein with reference to FIGS. 1-4.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, the present disclosure has been described herein in the context of a particular implementation in a particular environment for a particular purpose. Those of ordinary skill in the art will recognize the usefulness is not limited thereto and the present disclosure may be beneficially implemented in any number of environments for any number of purposes.

What is claimed is:

1. A method, comprising:
providing a first sensor, configured as a primary sensor in an active mode, and a second sensor, configured as a non-primary sensor in a standby mode, each associated with an orthopedic implant, wherein each of the first sensor and the second sensor includes an internal power source,
providing a controller operative to:
detect a triggering event via the primary sensor, and cause the internal power source of the non-primary sensor to transition from the standby mode to the active mode responsive to the triggering event being detected by the primary sensor;
providing the internal power source of the first sensor in the active mode and the internal power source of the second sensor in the standby mode;
detecting, by the first sensor, the triggering event;
activating, in response to the triggering event, the internal power source of the second sensor from the standby mode; and
detecting, by the second sensor, a characteristic associated with the orthopedic implant.

2. The method of claim 1, further comprising sending a sensor signal of the first sensor from the controller to a processor.

3. The method of claim 2, further comprising initiating, by the processor, a communication subroutine, the communication subroutine generating a message to send to an address.

4. The method of claim 1, further comprising sending a command signal from the processor to activate the internal power source of the second sensor, and initiating, in response to the command signal, a software download to at least one of the first sensor and the second sensor.

5. The method of claim 1, wherein the triggering event includes at least one of: a fall, a sudden acceleration or deceleration, a change in environment, a sleep state, a seizure, a change in pulse, a change in blood flow, a change in blood pressure, a change in compartment pressure, and a proximity to home base, and wherein the first sensor and the second sensor sense at least one of: acceleration, temperature, sound, infrared, pressure, pH, salinity, sodium, calcium, protein, bio markers, and a radio signal.

6. The method of claim 1, further comprising directly coupling to the orthopedic implant at least one of the first sensor and the second sensor.

7. The method of claim 1, further comprising returning the second sensor to the standby mode in response to a second triggering event.

8. The method of claim 1, wherein a patient property detected by the first sensor is different than the patient property detected by the second sensor.

9. The method of claim 1, wherein the first sensor is configured to detect the triggering event comprising a fall, and the second sensor is configured to become active responsive to the fall to collect post-fall data.

10. A system, comprising:
a first sensor, configured as a primary sensor in an active mode, and a second sensor, configured as a non-primary sensor in a standby mode, associated with one or more orthopedic implants;
a processor operable to receive a sensor signal from the first sensor in response to a triggering event;
a first internal power source of the first sensor and a second internal power source of the second sensor;
a controller associated with the first sensor and the second sensor, the controller operable to receive a command signal from the processor, the command signal operable to:
transition the second internal power source of the second sensor from the standby mode to the active mode responsive to the triggering event being detected by the first sensor; and
detect, by the second sensor, a characteristic of the one or more orthopedic implants.

11. The system of claim 10, wherein the triggering event includes at least one of: a fall, a sudden acceleration or deceleration, a change in environment, a sleep state, a seizure, a change in pulse, a change in blood flow, a change in blood pressure, a change in compartment pressure, and a proximity to home base, and wherein the first sensor and the second sensor sense at least one of: acceleration, temperature, sound, infrared, pressure, pH, salinity, sodium, calcium, protein, bio markers, and a radio signal.

12. The system of claim 10, wherein at least one of the first sensor and the second sensor is directly coupled to the one or more orthopedic implants.

13. The system of claim 10, wherein a patient property detected by the first sensor is different than the patient property detected by the second sensor.

14. The system of claim 10, wherein the first sensor is configured to detect the triggering event comprising a fall, and the second sensor is configured to become active responsive to the fall to collect post-fall data.

15. A method comprising:
providing a first sensor, configured as a primary sensor in an active mode, and a second sensor, configured as a non-primary sensor in a standby mode, each associated with a controller and one or more orthopedic implants, wherein the first sensor includes a first internal power source, and wherein the second sensor includes a second internal power source;
providing the first internal power source in the active mode and the second internal power source in the standby mode;
detecting, by the first sensor, a triggering event;
delivering, from the first sensor, a sensor signal to a processor in response to the triggering event;
transitioning, in response to a command signal from the processor responsive to the triggering event being detected by the first sensor, the second internal power source of the second sensor from the standby mode to the active mode; and
detecting, by the second sensor, a characteristic of the one or more orthopedic implants.

16. The method of claim 15, further comprising:
activating a transmitter of the second sensor in response to the command signal;
connecting the transmitter to an external computing device; and
delivering, from the external computing device, a communication regarding the triggering event or the characteristic of the one or more orthopedic implants.

17. The method of claim 15, further comprising initiating, in response to the command signal, a software download to at least one of the first sensor and the second sensor.

18. The method of claim 15, wherein the triggering event includes at least one of: a fall, a sudden acceleration or deceleration, a change in environment, a sleep state, a seizure, a change in pulse, a change in blood flow, a change in blood pressure, a change in compartment pressure, and a proximity to home base, and wherein the first sensor and the second sensor sense at least one of: acceleration, temperature, sound, infrared, pressure, pH, salinity, sodium, calcium, protein, bio markers, and a radio signal.

19. The method of claim 15, wherein a patient property detected by the first sensor is different than the patient property detected by the second sensor.

20. The method of claim 15, wherein the first sensor is configured to detect the triggering event comprising a fall, and the second sensor is configured to become active responsive to the fall to collect post-fall data.

\* \* \* \* \*